United States Patent [19]

Jojima et al.

[11] 4,279,908
[45] Jul. 21, 1981

[54] PYRIDAZINE DERIVATIVES AND THEIR USE AS AGRICULTURAL FUNGICIDES

[75] Inventors: Teruomi Jojima; Hideo Takeshiba, both of Hiromachi; Yukiyoshi Takahi, Shiga, all of Japan

[73] Assignee: Sankyo Company Limited, Tokyo, Japan

[21] Appl. No.: 137,779

[22] Filed: Apr. 7, 1980

[30] Foreign Application Priority Data

Apr. 19, 1979 [JP] Japan ................................ 54-48209
Apr. 19, 1979 [JP] Japan ................................ 54-48210

[51] Int. Cl.$^3$ .................... A01N 47/16; A01N 47/18; C07D 237/14; C07D 413/12
[52] U.S. Cl. ............................ 424/248.55; 424/250; 424/248.5; 544/82; 544/114; 544/238; 544/239
[58] Field of Search ................. 544/114, 82, 238, 239; 424/248.55, 248.5, 250

[56] References Cited

U.S. PATENT DOCUMENTS

| 2,624,730 | 1/1953 | Steck | 544/239 |
| 3,862,943 | 1/1975 | Houlihan | 544/239 |
| 4,052,395 | 10/1977 | Jojima et al. | 544/239 |

Primary Examiner—Henry R. Jiles
Assistant Examiner—R. W. Ramsuer
Attorney, Agent, or Firm—Frishauf, Holtz, Goodman & Woodward

[57] ABSTRACT 6-(3- And/or 5-halophenyl)pyridazines having an N-substituted carbamoyloxy, carbamoylthio, thiocarbamoyloxy or thiocarbamoylthio group at the 3-position on they pyridazine system and 6-(3- and/or 5-halophenyl)-3-pyridazone derivatives having a substituted or unsubstituted hydrocarbyloxycarbonyl substituent at the 2-position of the pyridazine ring have good fungicidal activity, making them useful as agricultural fungicides suitable for application to seeds, plants and agricultural land, and can be prepared by reacting the corresponding 6-substituted pyridazone or pyridazinethione with the corresponding carbamoyl halide or halocarbonate.

24 Claims, No Drawings

PYRIDAZINE DERIVATIVES AND THEIR USE AS AGRICULTURAL FUNGICIDES

BACKGROUND TO THE DISCLOSURE

The present invention relates to a series of new pyridazine derivatives having a halo-substituted phenyl group at the 6-position and either a carbamoyloxy group (or the corresponding group in which one or both of the oxygen atoms has been replaced by a sulphur atom) at the 3-position or a substituted or unsubstituted hydrocarbyloxycarbonyl group at the 2-position and an oxo group at the 3-position. The invention also provides a fungicidal composition comprising these compounds and useful as an agricultural fungicide and a method of treating seeds, growing plants and land to protect plants from fungal attack by applying one or more of the compounds of the invention thereto.

Although very many different types of compound are known for use as fungicides, and, in particular, for use as agricultural fungicides, there is a continuous demand for new agricultural fungicides. This demand is partly due to the continuous development of resistant strains of fungus, which require new chemicals to combat them, and partly due to the inability of some known fungicides to met all of the requirements imposed upon them.

For example, our UK Patent Specification No. 1,533,010 (U.S. Pat. No. 4,052,395) discloses a series of 6-(substituted phenyl)-pyridazone derivatives which have excellent fungicidal activity. However, although the fungicidal activity of the compounds claimed in our earlier Patent is excellent, they have the disadvantage that they are not readily biodegradable and this can, in some cases, give rise to problems if biologically active residues are left on the land or in cultivated produce.

Accordingly, notwithstanding the excellent fungicidal activity of the earlier compounds, there is a demand for compounds useful as agricultural fungicides which, whilst retaining much of the activity of the earlier compounds, have the advantage of being more readily biodegradable.

BRIEF SUMMARY OF INVENTION

It is, therefore, an object of the present invention to provide a new series of pyridazine derivatives which are useful as agricultural fungicides, whilst being more readily biodegradable than are the known compounds referred to above.

It is a further object of the invention to provide a fungicidal composition comprising, as active ingredient, one or more of the compounds of the invention in admixture with an agriculturally acceptable carrier or diluent.

It is a still further object of the invention to provide a method of controlling pathogenic fungi in plants, seeds or soil, in which there is applied to said plant, seed or soil or to a locus including said plant, seed or soil one or more of the compounds of the invention.

The new compounds of the present invention are those compounds of formulae (Ia) and (Ib):

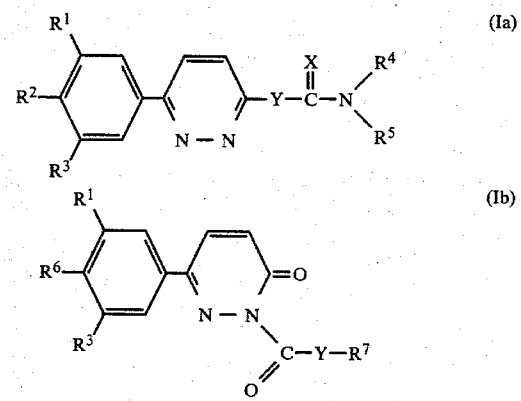

wherein:

$R^1$ and $R^3$ are the same or different and each represents a halogen atom, or one of $R^1$ and $R^3$ represents a halogen atom and the other represents a hydrogen atom;

$R^2$ represents a hydrogen atom, an alkyl group, an alkoxy group, a halogen atom or a group of formula

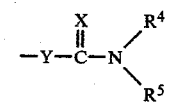

(wherein $R^4$ and $R^5$, X and Y are as defined below);

$R^4$ and $R^5$ are the same or different and each represents an alkyl group, a phenyl group, a phenyl group having one or more halogen and/or lower alkyl substituents, a benzyl group or a benzyl group having one or more halogen and/or lower alkyl substituents in the aromatic ring, or $R^4$ and $R^5$, together with the nitrogen atom to which they are attached, represent an optionally substituted nitrogen-containing heterocyclic ring;

$R^6$ represents a hydrogen atom, an alkyl group, an alkoxy group or a halogen atom; and $R^7$ represents an alkyl group, a phenyl group, a phenyl group having one or more halogen and/or lower alkyl substituents, a benzyl group or a benzyl group having one or more halogen and/or lower alkyl substituents in its aromatic ring.

DETAILED DESCRIPTION OF INVENTION

In the above formulae, where $R^1$, $R^2$, $R^3$ or $R^6$ represents a halogen atom, this may be a chlorine, bromine, fluorine or iodine atom, but is preferably a chlorine or bromine atom.

Where $R^2$, $R^4$, $R^5$ or $R^6$ represents an alkyl group, this may be a straight or branched chain alkyl group and is preferably a lower alkyl group having from 1 to 4 carbon atoms. Examples of suitable alkyl groups are methyl, ethyl, propyl, isopropyl, butyl and isobutyl groups, but the methyl group is preferred.

Where $R^2$ or $R^6$ represents an alkoxy group, this group may be a straight or branched chain group and is preferably a lower alkoxy group having from 1 to 4 carbon atoms, for example a methoxy, ethoxy, propoxy, isopropoxy, butoxy or isobutoxy group, of which the methoxy group is preferred.

Where $R^4$, $R^5$ or $R^7$ represents a phenyl group or a benzyl group having one or more halogen and/or lower alkyl substituents, we prefer that the group should have one or two substituents only. Preferred halogen substituents are chlorine or bromine atoms, most preferably chlorine atoms. Preferred lower alkyl substituents are groups having from 1 to 4 carbon atoms, most preferably a methyl group.

Where $R^4$ and $R^5$, together with the nitrogen atom to which they are attached, represent a nitrogen-containing heterocyclic group, this heterocyclic group preferably contains 5 or 6 ring atoms, which may contain one or more (preferably one) other hetero atoms in addition to the nitrogen atom already mentioned. Where such other hetero atoms are included, these are preferably oxygen and/or nitrogen. Examples of suitable heterocyclic groups are 1-pyrrolidinyl, piperidino, morpholino and 1-piperazinyl. Where the heterocyclic ring is substituted, there may be provided one or more (preferably one) substituents which are preferably hydrocarbon groups and most preferably lower alkyl (e.g. methyl) groups or phenyl groups. Particularly preferred substituted and unsubstituted heterocyclic groups are: 1-pyrrolidinyl, piperidino, morpholino, 1-piperazinyl, 4-methyl-1-piperazinyl and 4-phenyl-1-piperazinyl groups.

Where $R^7$ represents an alkyl group, this may be a straight or branched chain alkyl group and preferably has from 1 to 12 carbon atoms. Examples of such alkyl groups are the methyl, ethyl, propyl, isopropyl, butyl, isobutyl, pentyl, isopentyl, hexyl, octyl, nonyl, decyl and dodecyl groups. Of these groups, we prefer lower alkyl groups having from 1 to 4 carbon atoms, especially methyl, ethyl, butyl or isobutyl groups.

Of the compounds of formula (Ia), the most preferred compounds are those in which:

$R^1$ and $R^3$ are the same or different and each represents a chlorine or a bromine atom and $R^2$ represents a methyl group or a methoxy group; or $R^1$ represents a chlorine or bromine atom and $R^2$ and $R^3$ both represent hydrogen atoms; and $R^4$ and $R^5$ both represent methyl groups or $R^4$ and $R^5$, together with the nitrogen atom to which they are attached, represent a 1-pyrrolidinyl group, a piperidino group or a morpholino group; and X and Y both represent oxygen atoms.

The most preferred compounds of formula (Ib) are those in which:

$R^1$ and $R^3$ are the same or different and each represents a chlorine or a bromine atom, and $R^6$ represents a methyl group or a methoxy group; or $R^1$ represents a chlorine or bromine atom and $R^3$ and $R^6$ both represent hydrogen atoms; and, $R^7$ represents a lower alkyl group having from 1 to 4 carbon atoms or a benzyl group; and, Y represents an oxygen atom.

The following is a list of representative examples of the pyridazine derivatives of the present invention. The numbers appended to the compounds in this list are used hereinafter to identify the compounds.

1. 6-(3,5-Dichloro-4-methylphenyl)-3-N,N-dimethylcarbamoyloxypyridazine.
2. 6-(3,5-Dichloro-4-methylphenyl)-3-N,N-diethylcarbamoyloxypyridazine.
3. 6-(3,5-Dichloro-4-methylphenyl)-3-N,N-diisobutylcarbamoyloxypyridazine.
4. 6-(3-Bromo-5-chloro-4-methylphenyl)-3-(N-butyl-N-methylcarbamoyloxy)pyridazine.
5. 3-[N-sec-Butyl-N-(4-chlorobenzyl)carbamoyloxy]-6-(3,5-dichloro-4-methylphenyl)pyridazine.
6. 3-[N-(4-Chlorophenyl)-N-isopropylcarbamoyloxy]-6-(3,5-dichloro-4-methylphenyl)pyridazine.
7. 3-[N-(4-Chloro-2-methylphenyl)-N-methylcarbamoyloxy]-6-(3,5-dibromo-4-methylphenyl)pyridazine.
8. 6-(3,5-Dichloro-4-methylphenyl)-3-(1-pyrrolidinylcarbonyloxy)pyridazine.
9. 6-(3,5-Dichloro-4-methylphenyl)-3-(4-phenyl-1-piperazinylcarbonyloxy)pyridazine.
10. 6-(3,5-Dichloro-4-methylphenyl)-3-morpholinocarbonyloxypyridazine.
11. 6-(3-Chloro-4-methylphenyl)-3-morpholinocarbonyloxypyridazine.
12. 6-(3-Bromophenyl)-3-morpholinocarbonyloxypyridazine.
13. 6-(3,5-Dichloro-4-methoxyphenyl)-3-morpholinocarbonyloxypyridazine.
14. 6-(3,5-Dichloro-4-methylphenyl)-3-morpholino-(thiocarbonyl)oxypyridazine.
15. 6-(3,5-Dichloro-4-methylphenyl)-3-morpholinocarbonylthiopyridazine.
16. 6-(3,5-Dichloro-4-N,N-dimethylcarbamoyloxyphenyl)-3-N,N-dimethylcarbamoyloxypyridazine.
17. 6-(3,5-Dichloro-4-morpholinocarbonyloxyphenyl)-3-morpholinocarbonyloxypyridazine.
18. 6-(3,4-Dichlorophenyl)-3-N,N-dimethylcarbamoyloxypyridazine.
19. 6-(3-Chloro-4-methylphenyl)-3-N,N-dimethylcarbamoyloxypyridazine.
20. 6-(3-Bromophenyl)-3-N,N-dimethylcarbamoyloxypyridazine.
21. 6-(3,5-Dichloro-4-methoxyphenyl)-3-N,N-dimethylcarbamoyloxypyridazine.
22. 3-(N-Butyl-N-phenylcarbamoyloxy)-6-(3,5-dichloro-4-methylphenyl)pyridazine.
23. 6-(3,5-Dichloro-4-methylphenyl)-2-methoxycarbonyl-3-pyridazone.
24. 6-(3-Bromophenyl)-2-methoxycarbonyl-3-pyridazone.
25. 6-(3,4-Dichlorophenyl)-2-methoxycarbonyl-3-pyridazone.
26. 6-(3,5-Dichloro-4-methoxyphenyl)-2-methoxycarbonyl-3-pyridazone.
27. 6-(3,5-Dichloro-4-methylphenyl)-2-ethoxycarbonyl-3-pyridazone.
28. 6-(3-Bromophenyl)-2-ethoxycarbonyl-3-pyridazone.
29. 6-(3,5-Dichloro-4-methoxyphenyl)-2-ethoxycarbonyl-3-pyridazone.
30. 6-(3,5-Dichloro-4-methylphenyl)-2-ethylthiocarbonyl-3-pyridazone.
31. 6-(3,5-Dichloro-4-methylphenyl)-2-isopropoxycarbonyl-3-pyridazone.
32. 2-Butoxycarbonyl-6-(3,5-dichloro-4-methylphenyl)-3-pyridazone.
33. 6-(3-Bromophenyl)-2-butoxycarbonyl-3-pyridazone.
34. 2-Butoxycarbonyl-6-(3,4-dichlorophenyl)-3-pyridazone.
35. 2-Butoxycarbonyl-6-(3,5-dichloro-4-methoxyphenyl)-3-pyridazone.
36. 6-(3,5-Dichloro-4-methylphenyl)-2-isobutoxycarbonyl-3-pyridazone.
37. 6-(3,5-Dichloro-4-methylphenyl)-2-pentyloxycarbonyl-3-pyridazone.
38. 6-(3,5-Dichloro-4-methylphenyl)-2-hexyloxycarbonyl-3-pyridazone.

39. 6-(3,5-Dichloro-4-methylphenyl)-2-heptyloxycarbonyl-3-pyridazone.
40. 6-(3,5-Dichloro-4-methylphenyl)-2-octyloxycarbonyl-3-pyridazone.
41. 6-(3,5-Dichloro-4-methylphenyl)-2-nonyloxycarbonyl-3-pyridazone.
42. 2-Benzyloxycarbonyl-6-(3,5-dichloro-4-methylphenyl)-3-pyridazone.
43. 6-(3-Bromo-4-fluorophenyl)-2-(4-methylbenzyloxycarbonyl)-3-pyridazone.
44. 2-(2,4-Dichlorobenzyloxycarbonyl)-6-(3-iodophenyl)-3-pyridazone.
45. 6-(3,5-Dichloro-4-methylphenyl)-2-phenoxycarbonyl-3-pyridazone.
46. 2-(2-Chlorophenoxycarbonyl)-6-(3,5-dichloro-4-methylphenyl)-3-pyridazone.
47. 2-(4-Chloro-2-methylphenoxycarbonyl)-6-(3,4-dibromophenyl)-3-pyridazone.
48. 6-(3,5-Dichloro-4-methylphenyl)-2-propoxycarbonyl-3-pyridazone.
49. 6-(3Chloro-4-methylphenyl)-2-methoxycarbonyl-3-pyridazone.
50. 2-Butoxycarbonyl-6-(3-chloro-4-methylphenyl)-3-pyridazone.
51. 6-(3-Bromo-4-methylphenyl)-2-butoxycarbonyl-3-pyridazone.

Of the compounds listed above, particularly preferred compounds are Compounds Nos. 10, 12, 23, 27, 32, 33 and 42.

Compounds of formula (Ia) may be prepared by reacting a 6-(substituted phenyl)-3-pyridazone or 6-(substituted phenyl)-3-pyridazinethione of formula (II) with a carbamoyl chloride of formula (III) as shown in the following equation:

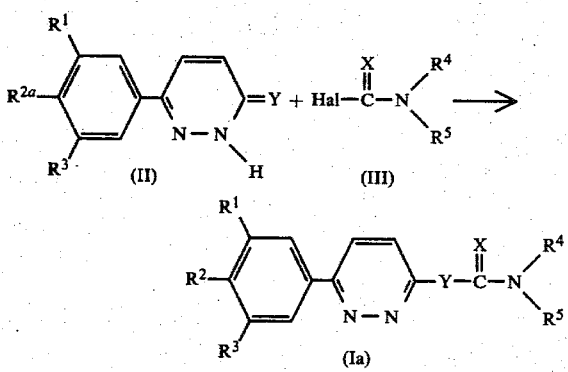

In the above formulae $R^{2a}$ represents any one of the groups previously defined for $R^2$ or a hydroxy group, Hal represents a halogen atom (preferably a chlorine atom), whilst $R^1$, $R^2$, $R^3$, $R^4$, $R^5$, X and Y are as defined above.

Compounds of formula (Ib) may be prepared by reacting a 6-(substituted phenyl)-3-pyridazone of formula (IV) with a halocarbonate or halothiocarbonate of formula (V), as shown by the following reaction equation:

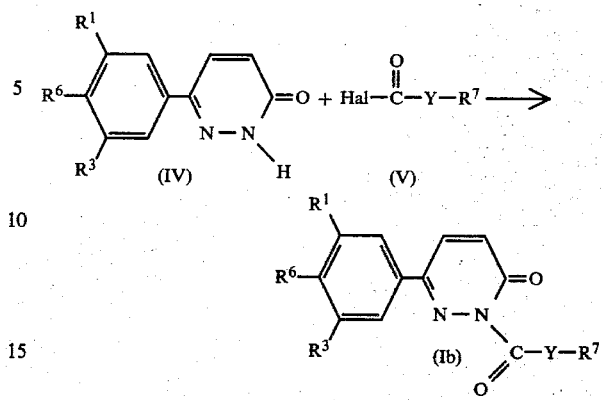

In the above formulae $R^1$, $R^3$, $R^6$, $R^7$, Y and Hal are as defined above and Hal preferably represents a chlorine atom.

The above reactions can easily be carried out simply by contacting the compound of formula (II) or (IV) with the compound of formula (III) or (V). We prefer that the two reagents in each reaction should be employed in equimolar amounts or that an excess of the compound of formula (III) or (V) should be employed.

The reaction can be carried out in the presence or absence of an inert solvent, although, in general we prefer that an inert solvent should be used. The nature of the solvent employed in the reaction is not critical, provided that it has no adverse effect on the reaction. Examples of suitable solvents include: aromatic hydrocarbons, such as benzene, toluene or xylene; ethers, such as diethyl ether, tetrahydrofuran or dioxan; ketones, such as acetone or methyl ethyl ketone; nitriles, such as acetonitrile or propionitrile; amides, such as dimethylformamide or dimethylacetamide; esters, such as ethyl acetate or ethyl propionate; dimethyl sulphoxide; or hexamethylphosphoric triamide (HMPA).

Where the compound of formula (III) or (V) is a liquid, this can act as the reaction solvent and, in this case, the use of an inert solvent is unnecessary, but the compound of formula (III) or (V) is preferably employed in large excess. However, it should be noted that, where the boiling point of the compound of formula (III) or (V) is low, the use of an inert solvent may be desirable, since otherwise it may be difficult to carry out the reaction at a sufficiently high temperature to achieve the desired rate of reaction.

The reaction temperature is, however, not critical and will normally be chosen to be between 0° C. and the temperature at which the reaction solvent refluxes, although, as is well known, higher reaction temperatures tend to improve reaction rates.

The reaction is preferably conducted in the additional presence of a base, which may be organic or inorganic. Examples of suitable bases include: tertiary amines, such as triethylamine, triethylenediamine, pyridine, N-methylmorpholine, 1,5-diazabicyclo[4.3.0]non-5-ene (DBN) or 1,5-diazabicyclo[5.4.0]undec-5-ene (DBU); alkali metal carbonates or bicarbonates, such as anhydrous sodium carbonate, anhydrous potassium carbonate or anhydrous sodium hydrogen carbonate; or alkali metal hydrides, such as lithium hydride, sodium hydride or potassium hydride.

As is well known, this type of reaction is preferably carried out without the presence of substantial quantities of water and hence it is preferred that, where alkali metal carbonates or bicarbonates are used as the base, these should be anhydrous. However, the presence of small quantities of water has no substantial adverse effect on the reaction and it is, therefore, possible to use commercial grade reagents which would normally be expected to contain minor quantities of water.

After completion of the reaction, the desired product may be recovered from the reaction mixture by conventional means, chosen having regard both to the nature of the product and to the reaction mixture from which it is to be separated. For example, where a volatile solvent has been used, this may be distilled off under reduced pressure and the residue extracted with a suitable organic solvent. The extract is then washed with water and dried with a suitable drying agent, after which the solvent is again distilled off. Where a hydrophilic solvent is employed for the reaction, the reaction mixture is first poured into water and then the mixture is extracted with a suitable water-immiscible organic solvent. The solvent is then distilled off from the extract, giving the desired compound as a crude product. This isolation technique is of particular value in the separation of compounds of formula (Ia).

Alternatively, where the product has precipitated, the precipitate is collected by filtration or, where the product has not precipitated, a water-immiscible solvent (e.g. hexane or petroleum ether) is added to the reaction mixture to cause it to precipitate and, again, the precipitate is collected by filtration. The resulting precipitate is washed and dried, giving the desired compound as a crude product. This technique is particularly useful in the separation of compounds of formula (Ib).

The resulting crude products may, if necessary, be further purified by conventional means, for example recrystallization or column chromatography.

The compounds of formula (II) in which Y represents an oxygen atom and the compounds of formula (IV), which are used as starting materials in the above reactions, may be prepared by the methods disclosed in the Journal of the American Chemical Society, 75, 1117 (1953), in U.K. Pat. Specification No. 1,533,010 and in U.S. Pat. Specification No. 4,052,395.

Those compounds of formula (II) in which Y represents a sulphur atom may easily be obtained by treating the corresponding compounds in which Y represents an oxygen atom which phosphorus pentasulphide.

The compounds of formula (Ia) and (Ib) may be employed as agricultural fungicides and show a preventive and curative effect against plant diseases, without damaging the host plants. They are also believed to have better systemic action (i.e. penetration of the compounds into and translocation of the compounds in the plant body) than the compounds of U.K. Pat. No. 1,533,010.

Specifically, they are particularly effective in the control of sheath blight, which is a very serious disease attacking rice plants; for this purpose, they are preferably employed in the form of a spray, particularly a foliar spray. They also effectively control damping-off, which is a fungus disease attacking various crops, such as beet, cotton plants and plants of the gourd family, and which is caused by pathogenic fungi of the class Rhizoctonia. They are also effective in the control of infectious soil-borne diseases, for example southern blight (which attacks the egg-plant and plants of the gourd family) and black scurf (which attacks potatoes); in this case, they are preferably employed in the form of a soil fungicide or a seed disinfectant.

At effective doses, the compounds of the invention do not exhibit any phytotoxicity to such plants as rice plants, tomato plants, potatoes, cotton plants, egg-plants, cucumbers and kidney beans. Moreover, they may be effectively used as fungicides in orchards, non-crop land and forests.

The compounds of the present invention may be formulated as preparations of the type commonly employed as agricultural fungicides, for example powdery dusts, coarse dusts, fine granules, coarse granules, wettable powders, emulsifiable concentrates, aqueous liquids, water-soluble powders and oil suspensions, by mixing them with a carrier and, if required, with another auxiliary agent or agents. The carrier employed may be natural or synthetic and organic or inorganic; it is mixed with the active compound to assist that compound to reach the material to be treated, and to make it easier to store, transport or handle the active compound.

Suitable solid carriers are: inorganic substances, such as clays (examples of which are kaolinite, montmorillonite and attapulgite), talc, mica, pyrophyllite, pumice, vermiculite, gypsum, calcium carbonate, dolomite, diatomaceous earth, magnesium carbonate, apatite, zeolite, silicic anhydride and synthetic calcium silicate; vegetable organic substances, such as soybean meal, tobacco powder, walnut powder, wheat flour, wood meal, starch and crystalline cellulose; synthetic or natural high molecular weight polymers, such as cumarone resins, petroleum resins, alkyd resins, polyvinyl chloride, polyalkylene glycols, ketone resins, ester gums, copal gum and dammar gum; waxes, such as carnauba wax and beeswax; or urea.

Examples of suitable liquid carriers are:
paraffinic or naphthenic hydrocarbons, such as kerosine, mineral oil, spindle oil and white oil, aromatic hydrocarbons, such as benzene, toluene, xylene, ethyl benzene, cumene and methylnaphthalene; chlorinated hydrocarbons, such as carbon tetrachloride, chloroform, trichloroethylene, monochlorobenzene and o-chlorotoluene; ethers, such as dioxan and tetrahydrofuran; ketones, such as acetone, methyl ethyl ketone, diisobutyl ketone, cyclohexanone, acetophenone and isophorone; esters, such as ethyl acetate, amyl acetate, ethylene glycol acetate, diethylene glycol acetate, dibutyl maleate and diethyl succinate; alcohols, such as methanol, hexanol, ethylene glycol, diethylene glycol, cyclohexanol, and benzyl alcohol; ether alcohols, such as ethylene glycol monoethyl ether, ethylene glycol monophenyl ether, diethylene glycol monoethyl ether and diethylene glycol monobutyl ether; other polar solvents, such as dimethylformamide or dimethyl sulphoxide; and water.

The fungicidal compositions of the present invention may contain surface active agents to emulsify, disperse wet, spread, bind, control disintegration, improve fluidity or rust-proof the fungicidal composition or to stabilize the active compound; although any of the conventional classes of surface active agent, be they non-ionic, anionic, cationic or amphoteric, may be employed, we prefer to employ non-ionic and/or anionic surface active agents. Examples of suitable non-ionic surface active agents are: the polymerization adducts of ethylene oxide with higher alcohols, such as lauryl alcohol, stearyl alcohol and oleyl alcohol; the polymerization adducts of ethylene oxide with alkylphenols, such as isooctylphenol or nonylphenol; the polymerization adducts of ethylene oxide with alkylnaphthols, such as butylnaphthol or octylnaphthol; the polymerization adducts of ethylene oxide with higher fatty acids, such as palmitic acid, stearic acid or oleic acid; the polymerization adducts of ethylene oxide with mono- or dialkylphosphoric acids, such as stearylphosphoric acid or dilaurylphosphoric acid; the polymerization adducts of ethylene oxide with amines, such as dodecylamine; the polymerization adducts of ethylene oxide with higher fatty acid amides, such as stearamide; the polymerization adducts of ethylene oxide with higher fatty acid esters of polyhydric alcohols, such as sorbitan, and said fatty acid esters; and the polymerization adducts of ethylene oxide with propylene oxide. Examples of suitable anionic surface active agents are alkyl sulphate salts, such as sodium lauryl sulphate or oleyl sulphate amine salt; alkyl sulphonate salts, such as sodium dioctyl sulphosuccinate or sodium 2-ethylhexene sulphonate; and aryl sulphonate salts, such as sodium isopropylnaphthalene sulphonate, sodium methylenebisnaphthalene sulphonate, sodium ligninsulphonate or sodium dodecylbenzene sulphonate.

Moreover, the agricultural fungicidal compositions of the present invention may be used in combination with high molecular weight compounds or other auxiliary agents, such as casein, gelatin, albumin, glue, sodium alginate, carboxymethylcellulose, methylcellulose, hydroxyethylcellulose or polyvinyl alcohol, in order to improve the properties and/or to increase the biological effect of the composition of the composition.

The above-mentioned carriers and various auxiliary agents may be used alone or in any desired combination, depending upon the type of preparation, the application and other factors.

In general, the fungicidal composition of the present invention may contain the active compound of formula (Ia) or (Ib) in an amount of from 0.1 to 99% by weight, based on the weight of the composition, although the precise amount of active ingredient in the composition will, naturally, depend upon the form of the composition and the manner in which it is to be applied.

For example, dusts may conveniently contain from 1 to 25% by weight of the active compound of formula (Ia) or (Ib), the remainder being a solid carrier.

Wettable powders may conveniently contain, for example, from 25 to 90% by weight of the active compound of formula (Ia) or (Ib), the remainder being a solid carrier and a dispersing and wetting agent, if required, together with a protective colloidal agent, a thixotropic agent and an anti-foaming agent.

Granules may conveniently contain from 1 to 35% by weight of the active compound of formula (Ia) or (Ib), a major portion of the remainder being a solid carrier. The active compound is homogeneously admixed with the solid carrier or is adhered or adsorbed onto the carrier surface; the diameter of each granule is preferably from 0.2 to 1.5 mm.

Emulsifiable concentrates may conveniently contain, for example, from 5 to 50% by weight of the active compound of formula (Ia) or (Ib) and from 5 to 20% by weight of an emulsifying agent, the remainder being a liquid carrier, together with, if required, a corrosion inhibitor.

The fungicidal compositions of the present invention, which are formulated into the various types of preparation described above, may be applied to a paddy or upland (dry) field in an amount of from 1 to 5,000 g, more preferably from 10 to 1,000 g, of the active compound of formula (Ia) or (Ib) per 10 ares for pre- or post-emergence fungicidal activity; they may be applied by foliage spraying, soil drenching, spraying onto irrigation water or any other known method.

The fungicidal composition of the present invention, when employed for seed disinfection or coating, may effectively control soil-borne or seed infectious diseases by coating seeds in an amount of from 0.1 to 2%, preferably from 0.2 to 0.5%, by weight of the active ingredient of formula (Ia) or (Ib), based on the weight of the seed.

The fungicidal compositions of the present invention may be blended with other fungicides for a broader fungicidal spectrum and, in some cases, a synergistic effect may be observed. Examples of other fungicides which may be employed in combination with the fungicidal composition of the present invention are: carbamate-type fungicides, such as 3,3'-ethylenebis-(tetrahydro-4,6-dimethyl-2$\underline{H}$-1,3,5-thiadiazine-2-thione), zinc or manganese ethylenebisdithiocarbamate, bis(dimethyldithiocarbamoyl)disulphide, zinc propylenebisdithiocarbamate, bis(dimethyldithiocarbamoyl) ethylene diamine, nickel dimethyldithiocarbamate, methyl 1-(butylcarbamoyl)-2-benzimidazolcarbamate, 1,2-bis(3-methoxycarbonyl-2-thioureido)benzene, 1-isopropylcarbamoyl-3-(3,5-dichlorophenyl)hydantoin, potassium N-hydroxymethyl-N-methyldithiocarbamate or 5-methyl-10-butoxycarbonylamino-10,11-dehydrodibenzo[b,f]azepine; pyridine-type fungicides, such as zinc bis[1-hydroxy-2(1$\underline{H}$)pyridinethionate] and sodium 2-pyridinethiol-1-oxide; phosphorus-containing fungicides, such as O,O-diisopropyl-S-benzylphosphorothioate and O-ethyl-S,S-diphenyldithiophosphate; phthalimide-type fungicides, such as N-(2,6-diethylphenyl)phthalimide and N-(2,6-diethylphenyl)-4-methylphthalimide; dicarboximide-type fungicides, such as N-trichloromethylthio-4-cyclohexene-1,2-dicarboximide and N-tetrachloroethylthio-4-cyclohexene-1,2-dicarboximide; oxazine-type fungicides, such as 5,6-dihydro-2-methyl-1,4-oxazine-3-carboxanilide-4,4-dioxide and 5,6-dihydro-b 2-methyl-1,4-oxazine-3-carboxanilide; naphthoquinone-type fungicides, such as 2,3-dichloro-1,4-naphthoquinone and 2-oxy-3-chloro-1,4-naphthoquinone copper sulphate adduct; and other fungicides, such as pentachloronitrobenzene, 1,4-dichloro-2,5-dimethoxybenzene, 5-methyl-s-triazole[3,4-b]benzthiazole, 2-(thiocyanomethylthio)benzthiazole, 3-hydroxy-5-methylisoxazole, N-(2,3-dichlorophenyl)tetrachlorophthalamidic acid, 5-ethoxy-3-trichloromethyl-1,2,4-thiadiazole, 2,4,6-trichloro-6-(o-chloroanilino)-1,3,5-triazine, 2,3-dicyano-1,4-dithioanthraquinone, copper 8-quinolate, polyoxin, validamycin, cycloheximide, iron methanearsonate, diisopropyl-1,3-dithioran-2-ylidene malonate, 3-allyloxy-1,2-benzoisothiazole 1,1-dioxide, kasugamycin, blasticidin S and 4,5,6,7-tetrachlorophthalide. However, the nature of such additional fungicides is not critical and, as is well-known in the art, provided there is no adverse inter-reaction, any other known fungicides may be employed.

The fungicidal compounds of the present invention may also be employed in admixture with various other agricultural or horticultural chemicals, including plant growth regulators, herbicides and insecticides. Examples of suitable plant growth regulators are: isourea-type plant growth regulators, such as N-methoxycarbonyl-N'-4-methylphenylcarbamoylethyl isourea and 1-(4- chlorophenylcarbamoyl)-3-ethoxycarbonyl-2-methyl isourea; sodium naphthyl acetate; 1,2-dihydropyridazine-3,6-dione; and the gibberellins.

Examples of herbicides which may be employed with the compounds of the invention are: triazine-type herbicides, such as 2-methylthio-4,6-bisethylamino-1,3,5-triazine, 2-chloro-4,6-bisethylamino-1,3,5-triazine, 4-ethylamino-6-isopropylamino-2-methoxy-1,3,5-triazine, 2-chloro-4-ethylamino-6-isopropylamino-s-triazine, 4,6-bis(isopropylamino)-2-methylthio-s-triazine or 4-ethylamino-6-isopropylamino-2-methylthio-s-triazine; phenoxy-type herbicides, such as 2,4-dichlorophenoxyacetic acid and its methyl, ethyl or butyl esters, 2-chloro-4-methylphenoxyacetic acid, 4-chloro-2-methylphenoxyacetic acid and ethyl 2-methyl-4-chlorophenoxybutyrate; diphenyl ether-type herbicides, such as 2,4,6-trichlorophenyl 4'-nitrophenyl ether, 2,4-dichlorophenyl 4'-nitrophenyl ether and 3,5-dimethylphenyl 4'-nitrophenyl ether; urea-type herbicides, such as 3-(3,4-dichlorophenyl)-1-methoxy-1-methylurea, 3-(3,4-dichlorophenyl)-1,1-dimethylurea and 3-(4-chlorophenyl)-1,1-dimethylurea, carbamate-type herbicides, such as 3-methoxycarbonylaminophenyl N-(3-methylphenyl)-carbamate, isopropyl N-(3-chlorophenyl)carbamate or methyl N-(3,4-dichlorophenyl)carbamate; uracil-type herbicides, such as 5-bromo-3-sec-butyl-6-methyluracil and 1-cyclohexyl-3,5-propyleneuracil; thiocarbamate-type herbicides, such as S-(4-chlorobenzyl)-N,N-diethylthiocarbamate, N-cyclohexyl-S-ethyl-N-ethylthiocarbamate, S-ethyl-hexahydro-1$\underline{H}$-azepine-1-carbothioate and S-ethyl-N,N-dipropylthiocarbamate; pyridinium salt herbicides, such as 1,1'-dimethyl-4,4'-bispyridinium dichloride; phosphorus-containing herbicides, such as N-(phosphonomethyl)glycine; aniline-type herbicides, such as $\alpha,\alpha,\alpha$-trifluoro-2,6-dinitro-N,N-dipropyl-p-toluidine, 4-(methylsulphonyl)-2,6-dinitro-N,N-dipropylaniline or $N^3,N^3$-diethyl-2,4-dinitro-6-trifluoromethyl-1,3-phenylenediamine; acid anilide-type herbicides, such as N-(butoxymethyl)-2-chloro-2',6'-diethylacetanilide, 2-chloro-2',6'-diethyl-N-(methoxymethyl)acetanilide and 3,4-dichloropropionanilide; pyrazole-type herbicides, such as 4-(2,4-dichlorobenzoyl)-5-hydroxy-1,3-dimethylpyrazole and 4-(2,4-dichlorobenzoyl)-1,3-dimethyl-5-(p-toluenesulphonyloxy)pyrazole; and other herbicides, such as 5-t-butyl-3-(2,4-dichloro-5-isopropoxyphenyl)-1,3,4-oxadiazolin-2-one, 4-chloro-2-[N-(4-chlorophenyl)-N-isopropylcarbamoyl]-5-methyl-4-isoxazolin-3-one, 3-isopropylbenzo-2-thia-1,3-diazinon-(4)-2,2-dioxide or 3-(2-methylphenoxy)pyridazine.

Suitable insecticides include: phosphorus-containing insecticides, such as O,O-diethyl O-(2-isopropyl-4-methyl-6-pyrimidinyl)phosphorothioate, O,O-diethyl S-[2-(ethylthio)ethyl]phosphorodithioate, O,O-dimethyl O-(3-methyl-4-nitrophenyl)thiophosphate, O,O-dimethyl S-(N-methylcarbamoylmethyl)phosphorodithioate, O,O-dimethyl S-(N-methyl-N-formylcarbamoylmethyl)phosphorodithioate, O,O-dimethyl S-[2-(ethylthio)ethyl]phosphorodithioate, O,O-diethyl S-[2-(ethylthio)ethyl]phosphorodithioate, O,O-dimethyl 1-hydroxy-2,2,2-trichloroethylphosphonate, O,O-diethyl O-(5-phenyl-3-isoxazolyl)phosphorothioate, methyl (4-bromo-2,5-dichlorophenyl)phenylphosphonothioate, O,O-dimethyl O-(3-methyl-4-methylcercaptophenyl)thiophosphate, O-ethyl-O-p-cyanophenyl phenylphosphonothioate, O,O-diethyl S-(1,2-dicarboethoxyethyl)phosphorodithioate, 2-chloro-1-(2,4,5-trichlorophenyl)vinyldimethyl phosphate, 2-chloro-1-(-b 2,4-dichlorophenyl)vinyldimethyl phosphate, O,O-dimethyl O-p-cyanophenyl phosphorothioate, 2,2-dichlorovinyl dimethyl phosphate, O,O-diethyl O-2,4-dichlorophenyl phosphorothioate, ethyl mercaptophenylacetate, O,O-dimethyl phosphorodithioate, S-[(6-chloro-2-oxo-3-benzoxazolinyl)methyl] O,O-diethylphosphorodithioate, 4-mercaptothiophenyl dipropylphosphate, 2-chloro-1-(2,4-dichlorophenyl)vinyl diethylphosphate, O,O-diethyl O-(3-oxo-2-phenyl-2$\underline{H}$-pyridazin-6-yl)phosphorothioate, O,O-dimethyl S-(1-methyl-2-ethylsulphinyl)ethyl phosphorothiolate, O,O-dimethyl S-phthalimidomethyl phosphorodithioate, dimethylmethylcarbamoylethylthioethyl thiophosphorothiolate, O,O-diethyl S-(N-ethoxycarbonyl-N-methylcarbamoylmethyl)phosphorodithioate, O,O-dimethyl S-[2-methoxy-1,3,4-thiadiazol-5(4$\underline{H}$)-onyl-(4)-methyl] dithiophosphate, 2-methoxy-4$\underline{H}$-1,3,2-benzodioxaphosphorin 2-sulphide, O,O-diethyl O-(3,5,6-trichloro-2-pyridyl)phosphorothioate, O-ethyl-O-2,4-dichlorophenyl thionobenzenephosphonate S-[4,6-diamino-s-triazin-2-ylmethyl] O,O-dimethyl phosphorodithioate, O-ethyl O-p-nitrophenyl phenylphosphorothioate, O,S-dimethyl-N-acetyl phosphoroamidothioate, 2-diethylamino-6-methylpyrimidin-4-yl diethylphosphorothioate, O,O-diethyl O-p-(methylsulphinyl)-phenyl phosphorothioate, O-ethyl S-propyl O-(2,4-dichlorophenyl)phosphorodithioate cis-3-(dimethoxyphosphinoxy)-N-methyl-cis-crotonamide or 2-diethylamino-6-methylpyrimidin-4-yl dimethylphosphorothioate; carbamate-type insecticides, such as 1-naphthyl N-methylcarbamate, S-methyl-N-[methylcarbamoyloxy]thioacetoimidate, m-tolyl methylcarbamate, 3,4-xylyl methylcarbamate, 3,5-xylyl methylcarbamate, 2-sec-butylphenyl N-methylcarbamate, 2,3-dihydro-2,2-dimethyl-7-benzofuranylmethylcarbamate, 2-isopropoxyphenyl-N-methylcarbamate, 1,3-bis(carbamoylthio)-2-(N,N-dimethylamino)propane hydrochloride and 2-diethylamino-6-methylpyrimidin-4-yl dimethylcarbamate; and other insecticides such as N,N-dimethyl-N'-(2-methyl-4-chlorophenyl)formamidine hydrochloride, nicotine sulphate, silbemycin, 6-methyl-2,3-quinoxalinedithiocyclic S,S-dithiocarbonate, 2,4-dinitro-6-sec-butylphenyl dimethylacrylate, 1,1-bis-(p-chlorophenyl-2,2,2-trichloroethanol, 2-(p-t-butylphenoxy)isopropyl-2'-chloroethyl sulphite, azoxybenzene, di-(p-chlorophenyl)cyclopropyl carbinol, di[tri(2,2-dimethyl-2-phenylethyl)tin] oxide, 1-(4-chlorophenyl)-3-(2,6-difluorobenzoyl)urea or S-tricyclohexyltin O,O-diisopropylphosphorodithioate.

The compositions of the invention may also be used together with control agents effective against rice blast, helminthosporium leaf spot, bacterial leaf blight, rice stem borers, planthoppers and/or leafhoppers, to save the labour involved in separate applications. A combination of one or more of the additional agents described above with the composition of the invention may be employed, depending upon the disease and/or insect to be controlled and the form of the composition to be employed. We particularly prefer to employ the composition of the invention in the form of a dust, for the control of rice plant diseases and/or for soil treatment.

In addition to the compounds listed above, it is also possible to incorporate fertilizers in the compositions of the invention.

The invention is further illustrated by the following Examples, of which Examples 1 to 7 illustrate the preparation of compounds of the invention, Example 8 illustrates the preparation of certain starting materials for use in the process of the invention, Examples 9 to 14 illustrate the preparation of compositions according to the invention and Examples 15 to 17 illustrate the biological activity of the compounds. In these Examples, all parts are by weight.

EXAMPLE 1

6-(3,5-Dichloro-4-methylphenyl)-3-N,N-dimethylcarbamoyloxypyridazine (Compound No. 1)

A mixture of 1.27 g of 6-(3,5-dichloro-4-methylphenyl)-3-pyridazone, 0.87 g of potassium carbonate, 1.3 g of N,N-dimethylcarbamoyl chloride and 50 ml of acetonitrile was heated under reflux for 14 hours. After cooling the reaction mixture, it was filtered and the filtrate was concentrated to one-fifth of its original volume by evaporation under reduced pressure, and was then extracted with chloroform. The solvent was distilled off under reduced pressure, giving a crude product which was then subjected to column chromatography through silica gel eluted with a 10:1 by volume mixture of benzene and ethyl acetate. There were obtained 0.9 g (55%) of the desired Compound No. 1, melting at 115°–117° C.

Elemental Analysis:
Calculated for $C_{14}H_{13}Cl_2N_3O_2$: C, 51.55%; H, 4.01%; Cl, 21.73%; N, 12.88%.
Found: C, 52.00%; H, 4.15%; Cl, 21.44%; N, 12.69%.
Infrared Absorption Spectrum (Nujol-Trade Mark) $\nu_{max}$ cm$^{-1}$: 1720 (carbamoyloxy)
Nuclear Magnetic Resonance Spectrum (CDCl$_3$) δ ppm:
2.50 (3H, singlet, 4-methyl on phenyl);
3.05, 3.18 (6H, singlet, N,N-dimethyl);
7.47, 7.88 (2H, AB-type quartet, J=9 cps, hydrogens at 4 and 5 positions on pyridazine);
7.96 (2H, singlet, hydrogens at 2 and 6 positions on phenyl).

Following the procedure described in Example 1, the following compounds were prepared and were obtained in yields varying from 9 to 100% of theory:
6-(3,5-Dichloro-4-methylphenyl)-3-N,N-diisobutylcarbamoyloxypyridazine (Compound No. 3) $n_D^{25}$=1.5613.
3-[N-sec-Butyl-N-(4-chlorobenzyl)carbamoyloxy]-6-(3,5-dichloro-4-methylphenyl)pyridazine (Compound No. 5) $n_D^{25.5}$=1.5882.
3-[N-(4-Chlorophenyl)-N-isopropylcarbamoyloxy]-6-(3,5-dichloro-4-methylphenyl)pyridazine (Compound No. 6) m.p.=159°–161° C.
6-(3,5-Dichloro-4-methylphenyl)-3-(1-pyrrolidinylcarbonyloxy)pyridazine (Compound No. 8) m.p.=145°–147° C.
6-(3,5-Dichloro-4-methylphenyl)-3-morpholinocarbonyloxypyridazine (Compound No. 10) m.p.=155°–159° C.
6-(3-Chloro-4-methylphenyl)-3-morpholinocarbonyloxypyridazine (Compound No. 11) m.p.=176°–177.5° C.
6-(3-Bromophenyl)-3-morpholinocarbonyloxypyridazine (Compound No. 12) m.p.=155°–158° C.
6-(3,5-Dichloro-4-methoxyphenyl)-3-morpholinocarbonyloxypyridazine (Compound No. 13) m.p.=143°–147° C.
6-(3,5-Dichloro-4-methylphenyl)-3-morpholino(thiocarbonyl)oxypyridazine (Compound No. 14) m.p.=165°–170° C.
6-(3,5-Dichloro-4-methylphenyl)-3-morpholinocarbonylthiopyridazine (Compound No. 15) m.p.=177°–179° C.

EXAMPLE 2

6-(3,5-Dichloro-4-methylphenyl)-3-morpholinocarbonyloxypyridazine (Compound No. 10)

1.27 g of 6-(3,5-dichloro-4-methylphenyl)-3-pyridazone and 1.12 g of triethylenediamine were suspended in 25 ml of acetonitrile, and then 1.5 g of morpholinocarbonyl chloride were added dropwise thereto. When the addition was complete, the mixture was stirred at room temperature for 30 minutes and then the white precipitate thus produced was removed by filtration. The filtrate was concentrated by evaporation under reduced pressure and then extracted with chloroform. The solvent was distilled under reduced pressure from the extract, giving a crude product which, after recrystallization from a mixture of benzene and hexene, gave 1.72 g (94%) of the desired Compound No. 10, melting at 155°–159° C.

Elemental Analysis:
Calculated for $C_{16}H_{15}Cl_2N_3O_3$: C, 52.19%; H, 4.10%; Cl, 19.25%; N, 11.41%.
Found: C, 52.44%; H, 4.07%; Cl, 19.35%; N, 11.33%.
Infrared Absorption Spectrum (Nujol) $\nu_{max}$ cm$^{-1}$: 1735 (carbamoyloxy).
Nuclear Magnetic Resonance Spectrum (CDCl$_3$) δ ppm:
2.50 (3H, singlet, 4-methyl on phenyl);
3.76 (8H, singlet, hydrogens on morpholino);
7.41, 7.83 (2H, AB-type quartet, J=9 cps, hydrogens at 4 and 5 positions on pyridazine);
7.92 (2H, singlet, hydrogens at 2 and 6 positions on phenyl).

Following the procedures described in Example 2, the following compounds were prepared and were obtained in yields from 9 to 100% of theory.
6-(3,5-Dichloro-4-methylphenyl)-3-N, N-dimethylcarbamoyloxypyridazine (Compound No. 1) m.p.=115°–117° C.
6-(3,5-Dichloro-4-methylphenyl)-3-N,N-diethylcarbamoyloxypyridazine (Compound No. 2) m.p.=88°–91.5° C.
6-(3,5-Dichloro-4-methylphenyl)-3-(4-phenyl-1-piperazinylcarbonyloxy)pyridazine (Compound No. 9) m.p.=202°–208° C.
6-(3,4-Dichlorophenyl)-3-N,N-dimethylcarbamoyloxypyridazine (Compound No. 18) m.p.=153°–155° C.
3-(N-Butyl-N-phenylcarbamoyloxy)-6-(3,5-dichloro-4-methylphenyl)pyridazine (Compound No. 22) m.p.=83°–86° C.

EXAMPLE 3

6-(3,5-Dichloro-4-methylphenyl)-3-morpholinocarbonyloxypyridazine (Compound No. 10)

1.27 g of 6-(3,5-dichloro-4-methylphenyl)-3-pyridazone and 1.12 g of triethylenediamine were dissolved in 25 ml of hexamethylphosphoric triamide, and then 1.5 g of morpholinocarbonyl chloride were added dropwise thereto. When the addition was complete, the mixture was stirred at room temperature for 1 hour and then poured into about 200 g of ice-water. The precipitate thus produced was collected by filtration, washed with water and dried, giving 1.75 g (94%) of the desired Compound No. 10. The melting point and spectroscopic data of this product agreed completely with those of the product obtained in Example 2.

EXAMPLE 4

6-(3,5-Dichloro-4-N,N-dimethylcarbamoyloxyphenyl)-3-N,N-dimethylcarbamoyloxypyridazine (Compound No. 16)

2.57 g of 6-(3,5-dichloro-4-hydroxyphenyl)-3-pyridazone and 3.36 g of triethylenediamine were suspended in 50 ml of acetonitrile, and then 3.21 g of N,N-dimethylcarbamoyl chloride were added dropwise thereto. When the addition was complete, the reaction mixture was stirred for 2 hours at room temperature and then the solvent was distilled under reduced pressure from the reaction mixture. The resulting residue was washed with water and dried, giving 3.8 g (95%) of the desired Compound No. 16, melting at 170°–172° C.

Elemental Analysis:

Calculated for $C_{16}H_{16}Cl_2N_4O_4$: C, 48.14%; H, 4.04%; Cl, 17.76%; N, 14.03%.

Found: C, 48.01%; H, 3.95%; Cl, 17.82%; N, 14.16%.

Infrared Absorption Spectrum (Nujol) $\nu_{max}$ cm$^{-1}$: 1720 (carbamoyloxy).

Nuclear Magnetic Resonance Spectrum (CDCl$_3$) δ ppm:
  3.18, 3.23 (12H, singlet, methylson carbamoyl groups);
  7.48, 7.89 (2H, AB-type quartet, J=9 cps, hydrogens at 4 and 5 positions on pyridazine);
  7.82 (2H, singlet, hydrogens at 2 and 6 position on phenyl).

Following the same procedure as was used in Example 4, the following compound was also prepared:
  6-(3,5-Dichloro-4-morpholinocarbonyloxyphenyl)-3-morpholinocarbonyloxypyridazine (Compound No. 17) m.p.=175°–177° C.

EXAMPLE 5

6-(3,5-Dichloro-4-methylphenyl)-2-methoxycarbonyl-3-pyridazone (Compound No. 23)

A mixture of 2.55 g of 6-(3,5-dichloro-4-methylphenyl)-3-pyridazone, 4.7 g of methyl chloroformate and 25 ml of xylene was heated under reflux for 1.5 hours. The reaction mixture was then left to cool at room temperature and the precipitate thus produced was collected by filtration and washed with hexane, giving 2.94 g (94%) of the desired Compound No. 23 in the form of colourless prisms having, after recrystallization from benzene, a melting point of 203°–206° C.

Infrared Absorption Spectrum (Nujol) $\nu_{max}$ cm$^{-1}$:
  1780 (methoxycarbonyl);
  1680 (carbonyl of pyridazone);
  1615 (<C=C>).

Elemental Analysis:
Calculated for $C_{13}H_{10}Cl_2N_2O_3$: C, 49.86%; H, 3.22%; Cl, 22.64%; N, 8.95%.

Found: C, 49.72%; H, 3.17%; Cl, 22.77%; N, 8.64%.

Following the same procedure as was used in Example 5, the following compounds were also produced and were obtained in yields of from 32 to 99% of theory:

6-(3-Bromophenyl)-2-methoxycarbonyl-3-pyridazone (Compound No. 24) m.p.=97°–100° C.
6-(3,4-Dichlorophenyl)-2-methoxycarbonyl-3-pyridazone (Compound No. 25) m.p.=170° C.
6-(3,5-Dichloro-4-methoxyphenyl)-2-methoxycarbonyl-3-pyridazone (Compound No. 26) m.p.=180°–185° C.
6-(3,5-Dichloro-4-methylphenyl)-2-ethoxycarbonyl-3-pyridazone (Compound No. 27) m.p.=172°–177° C.
6-(3-Bromophenyl)-2-ethoxycarbonyl-3-pyridazone (Compound No. 28) m.p.=88°–91° C.
6-(3,5-Dichloro-4-methoxyphenyl)-2-ethoxycarbonyl-3-pyridazone (Compound No. 29) m.p.=171°–176° C.
6-(3,5-Dichloro-4-methylphenyl)-2-ethylthiocarbonyl-3-pyridazone (Compound No. 30) m.p.=212°–220° C.
6-(3,5-Dichloro-4-methylphenyl)-2-isopropoxycarbonyl-3-pyridazone (Compound No. 31) m.p.=163°–169° C.
2-Butoxycarbonyl-6-(3,5-dichloro-4-methylphenyl)-3-pyridazone (Compound No. 32) m.p.=153°–157° C.
2-Butoxycarbonyl-6-(3,4-dichlorophenyl)-3-pyridazone (Compound No. 34) m.p.=107°–111° C.
2-Butoxycarbonyl-6-(3,5-dichloro-4-methoxyphenyl)-3-pyridazone (Compound No. 35) m.p.=142°–144° C.
6-(3,5-Dichloro-4-methylphenyl)-2-isobutoxycarbonyl-3-pyridazone (Compound No. 36) m.p.=159°–161° C.
6-(3,5-Dichloro-4-methylphenyl)-2-pentyloxycarbonyl-3-pyridazone (Compound No. 37) m.p.=144°–147° C.
6-(3,5-Dichloro-4-methylphenyl)-2-hexyloxycarbonyl-3-pyridazone (Compound No. 38) m.p.=128°–130° C.
6-(3,5-Dichloro-4-methylphenyl)-2-heptyloxycarbonyl-3-pyridazone (Compound No. 39) m.p.=130.5°–133° C.
2-Benzyloxycarbonyl-6-(3,5-dichloro-4-methylphenyl)-3-pyridazone (Compound No. 42) m.p.=180°–185.5° C.
6-(3,5-Dichloro-4-methylphenyl)-2-propoxycarbonyl-3-pyridazone (Compound No. 48) m.p.=170°–173° C.

EXAMPLE 6

2-Butoxycarbonyl-6-(3,5-dichloro-4-methylphenyl)-3-pyridazone (Compound No. 32)

A mixture of 2.55 g of 6-(3,5-dichloro-4-methylphenyl)-3-pyridazone and 6.8 g of butyl chloroformate was heated under reflux for 1 hour. The reaction mixture was then left to cool at room temperature and the precipitate produced was collected by filtration, washed with hexane and dried under reduced pressure, giving 3.3 g (93%) of the desired Compound No. 32 in the form of colourless plates melting at 153°–157° C.

Infrared Absorption Spectrum (Nujol) $\nu_{max}$ cm$^{-1}$:
  1775;
  1770 (butoxycarbonyl);
  1680 (carbonyl of pyridazone);
  1615 (>C=C<).

Nuclear Magnetic Resonance Spectrum (CDCl$_3$) δ ppm:
  0.8–2.2 (7H, multiplet, —CH$_2$CH$_2$CH$_3$);
  2.50 (3H, singlet, 4-methyl on phenyl);
  4.47 (2H, triplet, J=7 cps, —OCH$_2$—);
  6.98, 7.58 (2H, AB-type quartet, J=10 cps, Δ=31 cps, hydrogens at 4 and 5 positions of pyridazone);
  7.80 (2H, singlet, hydrogens at 2 and 6 positions of phenyl).

Elemental Analysis:

Calculated for $C_{16}H_{16}Cl_2N_2O_3$: C, 54.10%; H, 4.54%; Cl, 19.96%; N. 7.89%.

Found: C, 54.15%; H, 4.52%; Cl, 20.37%; H, 7.93%.

Following the same procedure as was used in Example 6, the following compounds were obtained in yields ranging from 32 to 99% of theory:

6-(3-Bromophenyl)-2-butoxycarbonyl-3-pyridazone (Compound No. 33) m.p.=67°–69° C.

6-(3,5-Dichloro-4-methylphenyl)-2-octyloxycarbonyl-3-pyridazone (Compound No. 40) m.p.=126°–129° C.

6-(3,5-Dichloro-4-methylphenyl)-2-nonyloxycarbonyl-3-pyridazone (Compound No. 41) m.p.=122°–125° C.

6-(3,5-Dichloro-4-methylphenyl)-2-phenoxycarbonyl-3-pyridazone (Compound No. 45) m.p.=140°–147° C.

EXAMPLE 7

2-Butoxycarbonyl-6-(3,5-dichloro-4-methylphenyl)-3-pyridazone (Compound No. 32)

A mixture of 2.55 g of 6-(3,5-dichloro-4-methylphenyl)-3-pyridazone, 1.43 g of butyl chloroformate, 1.75 g of potassium carbonate and 100 ml of acetonitrile was heated under reflux for 7.5 hours. After cooling the reaction mixture, the unreacted pyridazone and inorganic salts were removed by filtration and the solvent was distilled under reduced pressure from the filtrate. The residue was recrystallized from hexane, giving 1.1 g (31%) of the desired Compound No. 32, in the form of needles, whose melting point and spectroscopic data agreed completely with those of the compound obtained in Example 6.

EXAMPLE 8

6-(3,5-Dichloro-4-methylphenyl)-3(2H)pyridazinethione 12.75 g of 6-(3,5-dichloro-4-methylphenyl)-3-pyridazone and 22 g of phosphorus pentasulphide in 80 ml of pyridine were heated under reflux on an oil bath for 7 hours. The reaction mixture was then cooled to room temperature and its volume was reduced by one-half by distilling off the pyridine under reduced pressure. 300 ml of ethyl acetate were added to the residue and the mixture was poured into ice-water. After stirring the mixture for a short time, the resulting yellow solid was collected by filtration, washed with water and dried to give 7.5 g (56%) of the desired compound. After recrystallizing the compound from a 10:1 by volume mixture of ethanol and dioxan, the compound melted at 255°–258° C.

Elemental Analysis:

Calculated for $C_{11}H_8Cl_2N_2S$: C, 48.72%; H, 2.97%; Cl, 26.15%; N, 10.33%.

Found: C, 49.23%; H, 3.53%; Cl, 26.13%; N, 9.86%.

Following the same procedure as was used in Example 8, the following compound was also prepared:

6-(3-Bromophenyl)-3(2H)pyridazinethione m.p.=210°–212° C.

EXAMPLE 9

Dust 5 parts of Compound No. 14, 50 parts of talc and 45 parts of kaolin were uniformly mixed to form a dust.

EXAMPLE 10

Wettable Powder 50 parts of Compound No. 10, 29 parts of clay, 10 parts of diatomaceous earth, 5 parts of white carbon, 3 parts of sodium lignosulphonate, 2 parts of Newcol 1106 (a trade name of Nihon Nyukazai KK Japan) and 1 part of polyvinyl alcohol were uniformly mixed in a mixer and then pulverized 3 times by a hammer mill to give a wettable power.

EXAMPLE 11

Granules 70 parts of Compound No. 1 were finely pulverized, and 30 parts of clay were then added thereto. They were then mixed in a mixer to form a premix. 10 parts of this premix were uniformly mixed with 60 parts of clay and 30 parts of bentonite in a mixer. The mixture was kneaded with a suitable amount of water in a kneader, extruded through a screen having apertures of diameter 0.8 mm and dried in a draught drier at 50° C. The resulting product was formed into granules by means of a sifter.

EXAMPLE 12

Dust 5 parts of Compound No. 36, 50 parts of talc and 45 parts of kaolin were uniformly mixed to form a dust.

EXAMPLE 13

Wettable Powder 50 parts of Compound No. 29, 29 parts of clay, 10 parts of diatomaceous earth, 5 parts of white carbon, 3 parts of sodium lignosulphonate, 2 parts of Newcol 1106 and 1 part of polyvinyl alcohol were uniformly mixed in a mixer and then pulverized 3 times by a hammer mill to give a wettable powder.

EXAMPLE 14

Granules 70 parts of Compound No. 23 were finely pulverized, and then 30 parts of clay were added thereto. They were then mixed in a mixer to form a premix. 10 parts of this premix were uniformly mixed in a mixer with 60 parts of clay and 30 parts of bentonite. The mixture was kneaded with a suitable amount of water in a kneader, extruded through a screen having apertures of diameter 0.8 mm and dried in a draught drier at 50° C. The resulting product was formed into granules by means of a sifter.

The following Examples illustrate the use and activity of compounds according to the present invention. In these Examples, there were employed wettable powders, each containing 50% by weight of the active compound and prepared as described in Example 10.

EXAMPLE 15

Preventive effect against damping-off on cucumbers

The pathogenic fungus of damping-off (Rhizoctonia salani) was cultured on bran at 28° C. for 2 weeks and then homogeneously mixed with soil. The soil was placed in a pot having a diameter of 12 cm, and then 20 cucumber seeds of the variety Sagamihanpaku were sown thereon. The soil in the pot was then drenched with a test preparation containing one of the active compounds listed in following Table 1 in an amount of 250 ppm, at the rate of 3 liters of preparation per square meter of soil. The resulting pots were kept in a greenhouse at 25° C. for 2 weeks, after which the number of infected seedlings was determined. The results are summarized in Table 1.

Two pots, similarly prepared, were kept as controls and were not treated with any fungicidal preparations. The number of infected seedlings obtained from these pots is also reported in Table 1.

TABLE 1

| Compound No. | No. of infected seedlings | Compound No. | No. of infected seedlings |
|---|---|---|---|
| 11 | 7 | 34 | 7 |
| 12 | 5 | 38 | 12 |
| 23 | 8 | 39 | 11 |
| 24 | 7 | 40 | 8 |
| 25 | 8 | 41 | 11 |
| 26 | 5 | 42 | 8 |
| 27 | 9 | 45 | 12 |
| 28 | 5 | Control | 59 |
| 33 | 4 | Control | 58 |

EXAMPLE 16

Preventive effect on sheath blight of rice plants

Rice plant seedlings of the variety Koganenishiki at the 4-5 leaf stage were sprayed with a test preparation containing 30 ppm of one of the compounds listed in Table 2 in a total amount of 50 ml per 3 pots. The host plants were left at room temperature for 24 hours, and then 4-5 oat grains, on which the pathogenic fungus of sheath blight (*Pellicularia sasakii*) had previously been cultured, were placed around the root of each rice plant. The plants were then placed in a greenhouse maintained at 25°-27° C. and, 10 days after inoculation of the fungus, were examined for the degree of damage by determining the height of each lesion in centimeters. The results are shown in Table 2, in which the heights of the lesions are reported as averages over each group of 3 pots.

As a control, the same experiment was repeated twice, except that the seedlings were not treated with any fungicidal compound. These results are also shown in Table 2.

TABLE 2

| Compound No. | Height (cm) of lesion | Compound No. | Height (cm) of lesion |
|---|---|---|---|
| 1 | 1.6 | 30 | 0.9 |
| 2 | 2.1 | 31 | 0.4 |
| 8 | 1.4 | 32 | 0 |
| 10 | 0.8 | 33 | 1.4 |
| 11 | 2.6 | 34 | 2.0 |
| 12 | 1.5 | 35 | 0.6 |
| 13 | 1.3 | 36 | 0.5 |
| 14 | 1.0 | 37 | 0.7 |
| 18 | 1.6 | 38 | 1.3 |
| 22 | 1.8 | 39 | 1.0 |
| 23 | 0 | 40 | 0.8 |
| 24 | 1.4 | 41 | 1.3 |
| 25 | 1.5 | 42 | 0 |
| 26 | 1.9 | 45 | 1.0 |
| 27 | 0 | 48 | 0.3 |
| 28 | 1.5 | Control | 12.4 |
| 29 | 0.9 | Control | 12.8 |

EXAMPLE 17

Curative effect against sheath blight of rice plants

Rice plant seedlings of the variety Koganenishiki at the 6-7 leaf stage were infected with sheath blight by placing around the roots of each seedling 4-5 oat grains on which the pathogenic fungus of rice sheath blight (*Pellicularia sesakii*) had previously been cultured. The host plants were placed in a greenhouse at 25°-27° C. and then, 3 days after the inoculation (at which time the height of the lesion was measured), the host plants were removed from the greenhouse and each was sprayed with a test preparation containing 100 ppm of one of the compounds shown in following Table 3 in a total amount of 50 ml of the preparation per 3 pots. The plants were air-dried and then again placed in the greenhouse at 25°-27° C. 10 days after the application, the degree of disease was investigated by determining the increase in the height of the lesion (in centimeters) following application of the test preparation. The results obtained are shown in Table 3.

As a control, the experiment was repeated twice, except that the plants were not treated with any fungicidal compound. These results also are shown in Table 3.

TABLE 3

| Compound No. | Increase (cm) in lesion height | Compound No. | Increase (cm) in lesion height |
|---|---|---|---|
| 1 | 1.9 | 30 | 1.0 |
| 2 | 3.1 | 31 | 0.8 |
| 8 | 1.8 | 32 | 0.3 |
| 10 | 0.9 | 33 | 1.9 |
| 11 | 3.5 | 34 | 3.0 |
| 12 | 1.8 | 35 | 0.9 |
| 13 | 1.7 | 36 | 0.9 |
| 14 | 2.9 | 37 | 1.0 |
| 18 | 2.1 | 38 | 1.7 |
| 22 | 2.2 | 39 | 1.5 |
| 23 | 0.3 | 40 | 1.0 |
| 24 | 1.8 | 41 | 1.6 |
| 25 | 1.7 | 42 | 0.3 |
| 26 | 2.6 | 45 | 1.0 |
| 27 | 0.4 | 48 | 0.7 |
| 28 | 1.9 | Control | 16.1 |
| 29 | 1.1 | Control | 15.5 |

We claim:
1. Compounds of formulae (Ia) and (Ib):

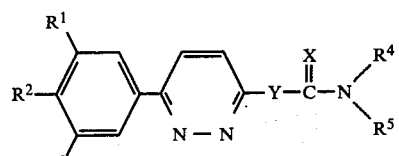 (Ia)

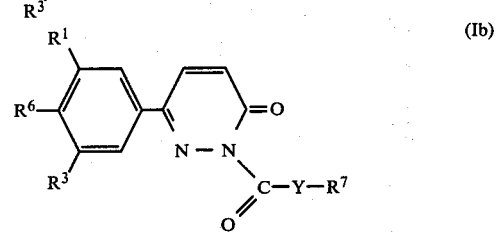 (Ib)

wherein:
R$^1$ and R$^3$ are the same or different and each represents a halogen atom, or one of R$^1$ and R$^3$ represents a halogen atom and the other represents a hydrogen atom;

R² represents a hydrogen atom, an alkyl group, an alkoxy group, a halogen atom or a group of formula

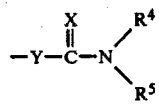

wherein R⁴, R⁵, X and Y are as defined below);

R⁴ and R⁵ are the same or different and each represents an alkyl group, a phenyl group, a phenyl group having one or more substituents selected from halogen atoms and lower alkyl groups, a benzyl group or a benzyl group having one or more substituents selected from halogen atoms and lower alkyl groups in its aromatic ring; or R⁴ and R⁵, together with the nitrogen atom to which they are attached, represent an optically substituted nitrogen-containing heterocyclic ring;

R⁶ represents a hydrogen atom, an alkyl group, an alkoxy group or a halogen atom;

R⁷ represents an alkyl group, a phenyl group, a phenyl group having one or more substituents selected from halogen atoms and lower alkyl groups, a benzyl group or a benzyl group having one or more substituents selected from halogen atoms and lower alkyl groups in the aromatic ring; and X and Y, which are the same or different, each represents an oxygen atom or a sulphur atom.

2. Compounds as claimed in claim 1, wherein R⁴, R⁵ and R⁷ are the same or different and each represents a lower alkyl group, a phenyl group, a phenyl group having one or two substituents selected from halogen atoms and methyl groups, a benzyl group or a benzyl group having one or two substituents selected from halogen atoms and methyl groups.

3. Compounds as claimed in claim 1, wherein R⁴ and R⁵, together with the nitrogen atom to which they are attached, represent a pyrrolidinyl group, a piperidino group, a morpholino group, a 1-piperazinyl group, a 4-methyl-1-piperazinyl group or a 4-phenyl-1-piperazinyl group.

4. Compounds as claimed in claim 1, wherein:

R¹ and R³ are the same or different and each represents a chlorine or bromine atom or one of R¹ and R³ represents a chlorine or bromine atom and the other represents a hydrogen atom;

R² represents a chlorine atom, a bromine atom, an alkyl group having from 1 to 4 carbon atoms or an alkoxy group having from 1 to 4 carbon atoms;

R⁴ and R⁵ are the same or different and each represents a phenyl group, a phenyl group having 1 or 2 substituents selected from chlorine atoms and methyl groups, a benzyl group or a benzyl group having 1 or 2 substituents selected from chlorine atoms and methyl groups; or R⁴ and R⁵, together with the nitrogen atom to which they are attached, represent a pyrrolidinyl group, a piperidino group, a morpholino group, a 1-piperazinyl group, a 4-methyl-1-piperazinyl group or a 4-phenyl-1-piperazinyl group;

R⁶ represents a chlorine atom, a bromine atom, an alkyl group having from 1 to 4 carbon atoms or an alkoxy group having from 1 to 4 carbon atoms; and R⁷ represents an alkyl group having from 1 to 12 carbon atoms, a phenyl group, a phenyl group having 1 or 2 substituents selected from chlorine atoms and methyl groups, a benzyl group or a benzyl group having 1 or 2 substituents selected from chlorine atoms and methyl groups.

5. Compounds of formula (Ia):

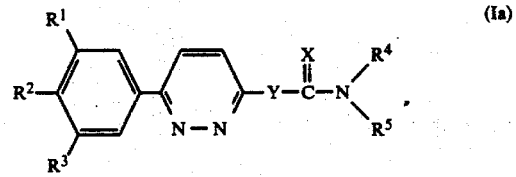

wherein:

R¹ and R³ are the same or different and each represents a chlorine atom or a bromine atom and R² represents a methyl group or a methoxy group; or R¹ represents a chlorine atom or a bromine atom and R² and R³ both represent hydroge atoms; and R⁴ and R⁵ both represent methyl groups or R⁴ and R⁵, together with the nitrogen atom to which they are attached, represent a pyrrolidinyl group, a piperidino group or a morpholino group; and X and Y both represent oxygen atoms.

6. Compounds of formula (Ib):

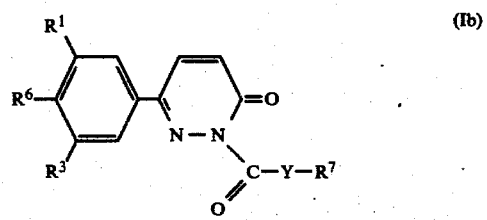

wherein:

R¹ and R³ are the same or different and each represents a chlorine atom or a bromine atom, and R⁶ represents a methyl group or a methoxy group; or R¹ represents a chlorine atom or a bromine atom and R³ and R⁶ both represent hydrogen atoms; and R⁷ represents an alkyl group having from 1 to 4 carbon atoms or a benzyl group; and Y represents an oxygen atom.

7. Compounds as claimed in claim 5, selected from:
6-(3,5-dichloro-4-methylphenyl)-3-morpholinocarbonyloxypyridazine and
6-(3-bromophenyl)-3-morpholinocarbonyloxypyridazine.

8. Compounds as claimed in claim 6, selected from:
6-(3,5-dichloro-4-methylphenyl)-2-methoxycarbonyl-3-pyridazone
6-(3,5-dichloro-4-methylphenyl)-2-ethoxycarbonyl-3-pyridazone
2-butoxycarbonyl-6-(3,5-dichloro-4-methylphenyl)-3-pyridazone
6-(3-bromophenyl)-2-butoxycarbonyl-3-pyridazone and
2-benzyloxycarbonyl-6-(3,5-dichloro-4-methylphenyl)-3-pyridazone.

9. A fungicidal composition comprising, as active ingredient an effective amount of a compound of formula (Ia) or (Ib) in admixture with an agriculturally or horticulturally acceptable carrier or diluent:

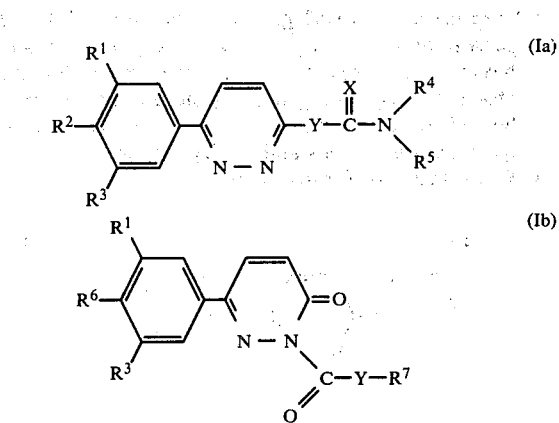

wherein:
R¹ and R³ are the same or different and each represents a halogen atom, or one of R¹ and R³ represents a halogen atom and the other represents a hydrogen atom;
R² represents a hydrogen atom, an alkyl group, an alkoxy group, a halogen atom or a group of formula

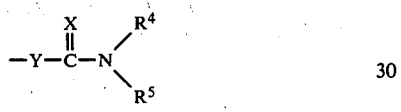

(wherein R⁴, R⁵, X and Y are as defined below);
R⁴ and R⁵ are the same or different and each represents an alkyl group, a phenyl group, a phenyl group having one or more substituents selected from halogen atoms and lower alkyl groups, a benzyl group or a benzyl group having one or more substituents selected from halogen atoms and lower alkyl groups in its aromatic ring; or
R⁴ and R⁵, together with the nitrogen atom to which they are attached, represent an optionally substituted nitrogen-containing heterocyclic ring;
R⁶ represents a hydrogen atom, an alkyl group, an alkoxy group or a halogen atom;
R⁷ represents an alkyl group, a phenyl group, a phenyl group having one or more substituents selected from halogen atoms and lower alkyl groups, a benzyl group or a benzyl group having one or more substituents selected from halogen atoms and lower alkyl groups in the aromatic ring; and
X and Y, which are the same or different, each represents an oxygen atom or a sulphur atom.

10. A fungicidal composition as claimed in claim 9, wherein, in said active ingredient:
R⁴, R⁵ and R⁷ are the same or different and each represents a lower alkyl group, a phenyl group, a phenyl group having one or two substituents selected from halogen atoms and methyl groups, a benzyl group or a benzyl group having one or two substituents selected from halogen atoms and methyl groups.

11. A fungicidal composition as claimed in claim 9, wherein, in said active ingredient:
R⁴ and R⁵, together with the nitrogen atom to which they are attached, represent a pyrrolidinyl group, a piperidino group, a morpholino group, a 1-piperazinyl group, a 4-methyl-1-piperazinyl group or a 4-phenyl-1-piperazinyl group.

12. A fungicidal composition as claimed in claim 9, wherein, in said active ingredient:
R¹ and R³ are the same or different and each represents a chlorine or bromine atom or one of R¹ and R³ represents a chlorine or bromine atom and the other represents a hydrogen atom;
R² represents a chlorine atom, a bromine atom, an alkyl group having from 1 to 4 carbon atoms or an alkoxy group having from 1 to 4 carbon atoms;
R⁴ and R⁵ are the same or different and each represents a phenyl group, a phenyl group having 1 or 2 substituents selected from chlorine atoms and methyl groups, a benzyl group or a benzyl group having 1 or 2 substituents selected from chlorine atoms and methyl groups; or
R⁴ and R⁵, together with the nitrogen atom to which they are attached, represent a pyrrolidinyl group, a piperidino group, a morpholino group, a 1-piperazinyl group, a 4-methyl-1-piperazinyl group or a 4-phenyl-1-piperazinyl group;
R⁶ represents a chlorine atom, a bromine atom, an alkyl group having from 1 to 4 carbon atoms or an alkoxy group having from 1 to 4 carbon atoms; and
R⁷ represents an alkyl group having from 1 to 12 carbon atoms, a phenyl group, a phenyl group having 1 or 2 substituents selected from chlorine atoms and methyl groups, a benzyl group or a benzyl group having 1 or 2 substituents selected from chlorine atoms and methyl groups.

13. A fungicidal composition as claimed in claim 9, wherein, in said compounds of formula (Ia),
R¹ and R³ are the same or different and each represents a chlorine atom or a bromine atom and R² represents a methyl group or a methoxy group; or
R¹ represents a chlorine atom or a bromine atom and R² and R³ both represent hydrogen atoms; and
R⁴ and R⁵ both represent methyl groups or R⁴ and R⁵, together with the nitrogen atom to which they are attached, represent a pyrrolidinyl group, a piperidino group or a morpholino group; and
X and Y both represent oxygen atoms.

14. A fungicidal composition as claimed in claim 9, wherein, in said compounds of formula (Ib),
R¹ and R³ are the same or different and each represents a chlorine atom or a bromine atom, and R⁶ represents a methyl group or a methoxy group; or
R¹ represents a chlorine atom or a bromine atom and R³ and R⁶ both represent hydrogen atoms; and
R⁷ represents an alkyl group having from 1 to 4 carbon atoms or a benzyl group; and
Y represents an oxygen atom.

15. A fungicidal composition as claimed in claim 9, wherein said active ingredient is selected from:
6-(3,5-dichloro-4-methylphenyl)-3-morpholinocarbonyloxypyridazine and
6-(3-bromophenyl)-3-morpholinocarbonyloxypyridazine.

16. A fungicidal composition as claimed in claim 9, wherein said active ingredient is selected from:
6-(3,5-dichloro-4-methylphenyl)-2-methoxycarbonyl-3-pyridazone
6-(3,5-dichloro-4-methylphenyl)-2-ethoxycarbonyl-3-pyridazone
2-butoxycarbonyl-6-(3,5-dichloro-4-methylphenyl)-3-pyridazone 6-(3-bromophenyl)-2-butoxycarbonyl-3-pyridazone and 2-benzyloxycarbonyl-6-(3,5-dichloro-4-methylphenyl)-3-pyridazone.

17. A method of controlling pathogenic fungi in plants, seeds or soil, in which there is applied to the plants, seeds or soil or to a locus containing the plants, seeds or soil an effective amount of a compound of formula (Ia) or (Ib):

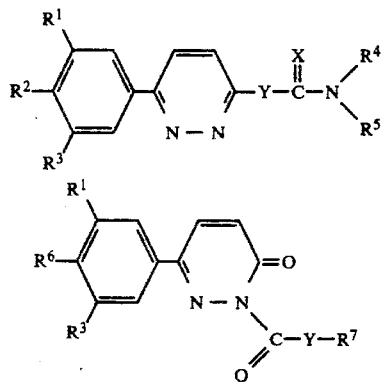

wherein:

$R^1$ and $R^3$ are the same or different and each represents a halogen atom, or one of $R^1$ and $R^3$ represents a halogen atom and the other represents a hydrogen atom;

$R^2$ represents a hydrogen atom, an alkyl group, an alkoxy group, a halogen atom or a group of formula

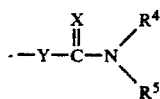

(wherein $R^4$, $R^5$, X and Y are as defined below);

$R^4$ and $R^5$ are the same or different and each represents an alkyl group, a phenyl group, a phenyl group having one or more substituents selected from halogen atoms and lower alkyl groups, a benzyl group or a benzyl group having one or more substituents selected from halogen atoms and lower alkyl groups in its aromatic ring; or $R^4$ and $R^5$, together with the nitrogen atom to which they are attached, represent an optionally substituted nitrogen-containing heterocyclic ring;

$R^6$ represents a hydrogen atom, an alkyl group, an alkoxy group or a halogen atom;

$R^7$ represents an alkyl group, a phenyl group, a phenyl group having one or more substituents selected from halogen atoms and lower alkyl groups, a benzyl group or a benzyl group having one or more substituents selected from halogen atoms and lower alkyl groups in the aromatic ring; and X and Y, which are the same or different, each represents an oxygen atom or a sulphur atom.

18. A method as claimed in claim 17, wherein, in said compound:

$R^4$, $R^5$ and $R^7$ are the same or different and each represents a lower alkyl group, a phenyl group, a phenyl group having one or two substituents selected from halogen atoms and methyl groups, a benzyl group or a benzyl group having one or two substituents selected from halogen atoms and methyl groups.

19. A method as claimed in claim 17, wherein, in said compound:

$R^4$ and $R^5$, together with the nitrogen atom to which they are attached, represent a pyrrolidinyl group, a piperidino group, a morpholino group, a 1-piperazinyl group, a 4-methyl-1-piperazinyl group or a 4-phenyl-1-piperazinyl group.

20. A method as claimed in claim 17, wherein, in said compound:

$R^1$ and $R^3$ are the same or different and each represents a chlorine or bromine atom or one of $R^1$ and $R^3$ represents a chlorine or bromine atom and the other represents a hydrogen atom;

$R^2$ represents a chlorine atom, a bromine atom, an alkyl group having from 1 to 4 carbon atoms or an alkoxy group having from 1 to 4 carbon atoms;

$R^4$ and $R^5$ are the same or different and each represents a phenyl group, a phenyl group having 1 or 2 substituents selected from chlorine atoms and methyl groups, a benzyl group or a benzyl group having 1 or 2 substituents selected from chlorine atoms and methyl groups; or $R^4$ and $R^5$, together with the nitrogen atom to which they are attached, represent a pyrrolidinyl group, a piperidino group, a morpholino group, a 1-piperazinyl group, a 4-methyl-1-piperazinyl group or a 4-phenyl-1-piperazinyl group;

$R^6$ represents a chlorine atom, a bromine atom, an alkyl group having from 1 to 4 carbon atoms or an alkoxy group having from 1 to 4 carbon atoms; and $R^7$ represents an alkyl group having from 1 to 12 carbon atoms, a phenyl group, a phenyl group having 1 or 2 substituents selected from chlorine atoms and methyl groups, a benzyl group or a benzyl group having 1 or 2 substituents selected from chlorine atoms and methyl groups.

21. A method as claimed in claim 17, wherein, in said compounds of formula (Ia), $R^1$ and $R^3$ are the same or different and each represents a chlorine atom or a bromine atom and $R^2$ represents a methyl group or a methoxy group; or $R^1$ represents a chlorine atom or a bromine atom and $R^2$ and $R^3$ both represent hydrogen atoms; and $R^4$ and $R^5$ both represent methyl groups or $R^4$ and $R^5$, together with the nitrogen atom to which they are attached, represent a pyrrolidinyl group, a piperidino group or a morpholino group; and X and Y both represent oxygen atoms.

22. A method as claimed in claim 17, wherein, in said compounds of formula (Ib), $R^1$ and $R^3$ are the same or different and each represents a chlorine atom or a bromine atom, and $R^6$ represents a methyl group or a methoxy group; or $R^1$ represents a chlorine atom or a bromine atom and $R^3$ and $R^6$ both represent hydrogen atoms; and $R^7$ represents an alkyl group having from 1 to 4 carbon atoms or a benzyl group; and Y represents an oxygen atom.

23. A method as claimed in claim 17, wherein said compound is selected from:

6-(3,5-dichloro-4-methylphenyl)-3-morpholinocarbonyl-oxypyridazine and 6-(3-bromophenyl)-3-morpholinocarbonyloxypyridazine.

24. A method as claimed in claim 17, wherein said compound is selected from:
- 6-(3,5-dichloro-4-methylphenyl)-2-methoxycarbonyl-3-pyridazone
- 6-(3,5-dichloro-4-methylphenyl)-2-ethoxycarbonyl-3-pyridazone
- 2-butoxycarbonyl-6-(3,5-dichloro-4-methylphenyl)-3-pyridazone
- 6-(3-bromophenyl)-2-butoxycarbonyl-3-pyridazone and
- 2-benzyloxycarbonyl-6-(3,5-dichloro-4-methylphenyl)-3-pyridazone.